United States Patent [19]
Manni et al.

[11] Patent Number: 5,225,001
[45] Date of Patent: Jul. 6, 1993

[54] SINGLE CHANNEL SCOPE CLEANING METHOD AND APPARATUS

[75] Inventors: Jeffrey G. Manni, Burlington, Mass.; Timothy Silva, Grass Valley, Calif.

[73] Assignee: Healthtek, Nevada City, Calif.

[21] Appl. No.: 585,848

[22] Filed: Sep. 19, 1990
(Under 37 CFR 1.47)

[51] Int. Cl.$^5$ .................................................. B08B 3/02
[52] U.S. Cl. ................................ 134/22.12; 134/104.1; 134/167 C;169 C; 128/4
[58] Field of Search ............ 134/166 C, 167 C:168 C, 134/169 C, 22.11, 22.12, 104.1; 128/4; 15/250 R, 321; 239/284.1

[56] References Cited

U.S. PATENT DOCUMENTS

| | | | |
|---|---|---|---|
| 3,437,747 | 4/1969 | Sheldon | 128/4 X |
| 3,830,225 | 8/1974 | Shinnick | 128/4 |
| 3,841,330 | 10/1974 | Storz | 128/4 X |
| 4,132,227 | 1/1979 | Ibe | 128/4 |
| 4,281,646 | 8/1981 | Kinoshita | 134/113 |
| 4,598,698 | 7/1986 | Siegmund | 128/4 |
| 4,667,691 | 5/1987 | Sasa | 134/169 C |
| 4,860,731 | 8/1989 | Matsurra | 128/4 X |
| 4,881,523 | 11/1989 | Heckele | 128/4 |
| 4,973,311 | 11/1990 | Iwakoshi et al. | 128/4 |
| 4,991,565 | 2/1991 | Takahashi et al. | 128/4 |

Primary Examiner—Frankie L. Stinson
Attorney, Agent, or Firm—Lyon & Lyon

[57] ABSTRACT

A scope cleaning apparatus and method including a device containing a cleansing solution. An actuating mechanism is provided for passing the solution through flexible tubing coupled to a scope cleaning device. The scope cleaning device includes an elongate sleeve adapted for positioning over and in general coaxial and concentric alignment with the elongate body of the scope or as a parallel tube. The proximal end of the sleeve includes a coupler for detachably coupling to the scope adjacent the eye piece thereof, with the distal end of the sleeve having an aperture therein, with the length of the sleeve being sufficient for termination of the distal end in proximate relation to the lens of the scope. The coupler includes provision for attachment to the solution delivery tubing for enabling passage of the solution into a single fluid passage, which may be annular or parallel, defined between the scope body and the cleaner sleeve. The syringe is actuated through irrigation and aspiration cycles for passage of solution out of, and into, the annular fluid flow path, with the duration of the irrigation cycle preferably being greater than the aspiration cycle.

4 Claims, 2 Drawing Sheets

SINGLE CHANNEL SCOPE CLEANING METHOD AND APPARATUS

This invention relates to a method and apparatus for maintaining a clean environment in the area near the distal end of a surgical scope, such as those used in endoscopy and arthroscopy. More particularly, this invention is directed to a single channel scope cleaning method and apparatus.

In modern surgical practices, a small diameter elongate tube may include provision for viewing the surgical field, such as those devices utilized in arthroscopy and endoscopy. The scope devices include a lens system or fiberoptic encased within the small diameter tube, which devices serve as viewing means for observation of the surgery being performed through small perforation size incisions rather than large open incisions.

In such procedures, laser devices may be employed in proximity to the viewing device, with the cutting process creating smoke and fumes as well as other debris, which cloud the viewing end.

Accordingly, in accordance with an aspect of the invention, an uncomplicated, relatively inexpensive, new and improved scope cleaning method and apparatus is provided.

SUMMARY OF THE INVENTION

The foregoing and other objects of the invention are, in a specific and preferred embodiment thereof, accomplished by providing a scope cleaning method and apparatus which include a syringe device containing the cleansing fluid, with the syringe being positioned within a stepper motor actuated or other type of metering mechanism, e.g., a solenoid, the cleansing fluid being passed through a tubing coupled to a scope cleaning device. The scope cleaning device includes an elongated sleeve, which may be rigid or flexible, adapted for positioning over and in generally parallel or coaxial alignment with the elongated fiberoptic member of the scope which also may be rigid or flexible to create a single channel cleaning apparatus. The proximal end of the sleeve includes a coupler for detachably coupling to the scope adjacent the eye piece thereof, with the other distal end of the sleeve being provided with an opening aligned with the lens of the fiberoptic member, with the length of the sleeve being sufficient for termination of the distal end thereof beyond and in spaced, but substantially close, relation to the lens of the scope. The coupler includes provision for attachment to the tubing which delivers the cleaning solution and a solution flow path for enabling passage of the solution into the annular path defined between the scope lens tube and the sleeve. The stepper motor which apparatus the syringe is actuated through irrigation and aspiration cycles for passage of solution into and out of the annular fluid flow path, with the duration of the irrigation cycle preferably exceeding that of the aspiration cycle by a modest amount such that a minimal amount of cleaning solution is left in the patient. In this manner, an excess of solution is passed over the lens at the distal end of the sleeve and upon withdrawal of the syringe plunger, a part of the solution is withdrawn, the timing being such that substantially all of the debris in the vicinity of the lens is removed and the withdrawn or aspirated solution is essentially clean solution.

Other objects, features and advantages will become apparent from a reading of the following specification, when taken in conjunction with the drawings, wherein like reference numerals refer to like elements in the several views.

BRIEF DESCRIPTION OF THE DRAWINGS

FIG. 3 is an enlarged fragmentary view, partially broken away, showing the coupler portion and the proximal end of the cleaner sleeve of the apparatus of FIG. 1;

FIG. 5 is an enlarged fragmentary view of the distal ends of the cleaner sleeve and the fiberoptic member.

DETAILED DESCRIPTION OF THE PREFERRED EMBODIMENT

Figure 1:
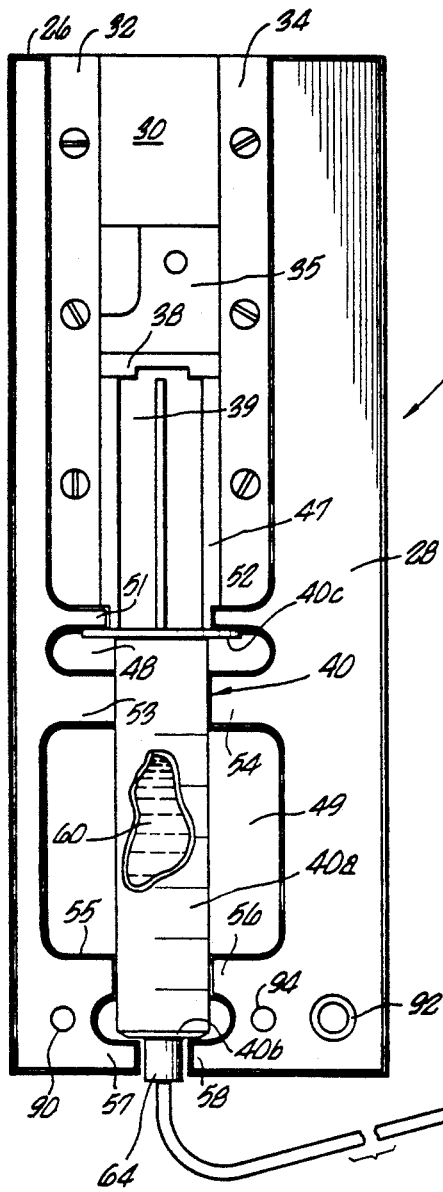
FIG. 1 is a perspective view of the scope cleaner apparatus in accordance with the invention, partially broken away.

Referring now to the drawings, and particularly to FIG. 1 there is shown a scope cleaner apparatus, which includes a syringe actuator, generally designated 10, and a scope cleaner device, generally designated 12. The scope cleaner device 12 is shown attached to a scope 14, which may be an endoscopic device or an arthroscopic device or other similar device. The scope device 14 includes an elongate fiberoptic member 16 of relatively small diameter through which a fiberoptic light is passed (See also FIGS. 2 and 3), the distal end of the cleaner sleeve 72 being designated 18. The scope 14 includes a handle end 20 with a block-shaped junction portion 22 intermediate the fiberoptic member 16 and handle 20. In some scopes, the portion 22 includes provision for attachment to an external viewing device, such as a television monitor (not shown).

Referring specifically to FIG. 1, the syringe actuator 10 has lateral opposing elongate generally bar-shaped frame members 26, 28, with the inner facing edges thereof configured for receiving therein a stepper motor 30 at the upper end thereof, the stepper motor 30 being mounted and connected between facing upper inner edges of the frame member 26, 28 by longitudinally extending straps 32, 34. As can be seen, the actuator 35 of the stepper motor 30 depends below the stepper motor 30 along the longitudinal centerline between the facing inner edges of frame members 26, 28. The lower end of actuator 35 is configured for receiving the flanged end 38 of the plunger 39 of a syringe, generally designated 40.

The body 40a of the syringe 40 is of cylindrical configuration with a tapered or funnel like lower end 40b, with the upper end of the syringe body including an outwardly extending flange portion 40c. The inner facing edges of the frame members 26, 28 are configured for receiving the syringe 40 therein. For this purpose, the inner facing edges are configured for defining a syringe plunger opening 47, a flange opening 48 and a syringe body opening 49. The openings 47 and 48 are bounded by inwardly extending aligned spaced projections 51, 52, the lower edges of which abut against the upper surfaces of the flange portion 40c of syringe 40.

Intermediate openings 48 and 49, a second pair of inwardly extending aligned projections 53, 54 terminate in spaced relation, the spacing being slightly greater than the diameter of the syringe body 40a. The opening 49 is of enlarged rectangular configuration with the lower end being bounded by a pair of aligned inwardly extending projections 55, 56 having a spacing similar to that of the projections 53, 54, that is, a spacings lightly greater than the diameter of the body 40a. The lower end of the frame members 26, 28 are configured for defining a seat for abutting coaction with the discharge end 40b of the syringe 40. This seat is accomplished by a fourth pair of inwardly extending aligned projections 57, 57 which terminate in spaced relation a distance less than the diameter of the body 40a, and greater than the diameter of fitting 64 attached to the outlet end of the syringe 40.

The syringe 40 is held frictionally within the openings of the syringe actuator 10 by pressing the body 40a of the syringe 40 into the respective openings so that the flange 40c abuts the underside of the inwardly extending projections 51, 52, with the discharge end 40b of the syringe 40 abutting the seat formed by projections 57, 58. Upon insertion of the syringe 40 into the actuator 10, with the syringe filled with solution 60, the plunger 39 is fully withdrawn out of the body with the upper end 38 of plunger 39 in abutting engagement with the lower end of the stepper motor actuator 35.

An appropriate lens cleaning sterile solution 60 is contained within body 40a of the syringe 40. The lens cleaning solution 60 is delivered, via solution delivery tubing 62, which includes a fitting 64 at one end for frictional attachment to the outlet end of the syringe 40. The other end of the tubing 62 has a fitting 66 for coupling to another mating fitting 68 (See FIG. 2) on the coupler 70 of the cleaner device 12.

Figure 2:
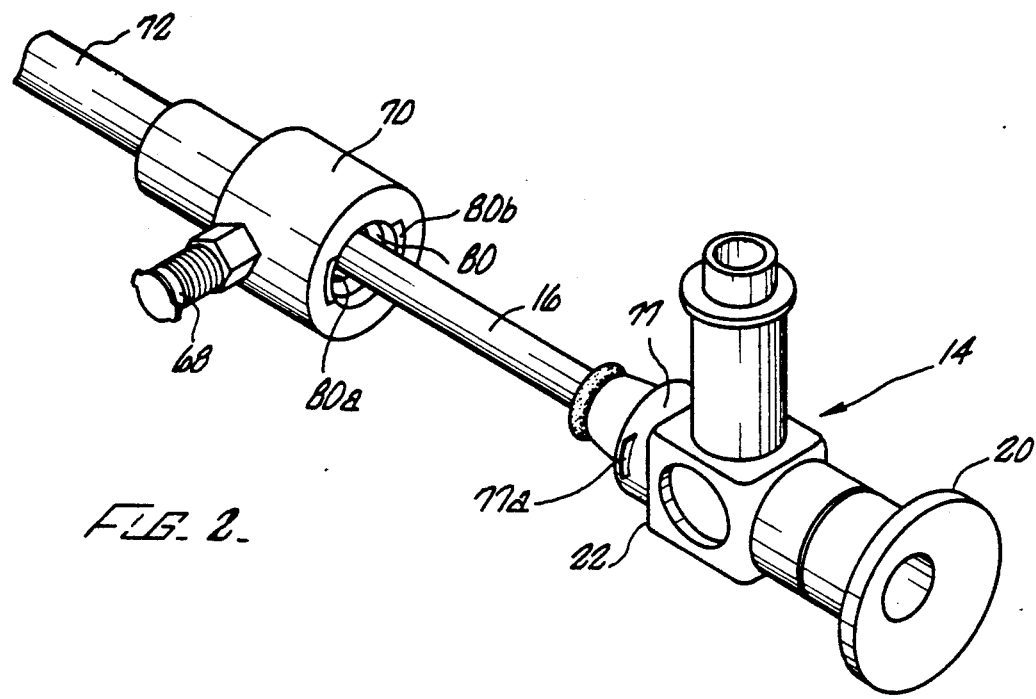
FIG. 2 is an exploded fragmentary perspective view of the apparatus of FIG. 1 illustrating the coupler interconnection of the scope cleaner sleeve to the scope.

Referring now to FIG. 1, 2 and 3, the scope cleaner device 12 will be described in detail. The device 12 includes coupler 70 which is an enlarged cylindrically configured portion fixedly coupled to an elongate sleeve member 72 to form a single annular passage 74 between sleeve 72 and lens tube 16. Alternatively, sleeve 72 may be a separate, generally parallel tube positioned adjacent to the fiberoptic member 16. Preferably, an o-ring or other sealing device is used to assure an effective seal between coupler 70 and sleeve member 72. The block portion 22 of the scope 14 is configured for detachably mating with the coupler 70 by provision of a male coupling portion 77 which is a cylindrically configured body with diametrically opposed tabs, one of which is shown as 77a, extending therefrom. The tabs are configured for being matingly received within a female coupling portion 80 formed in the face of coupler 70, the portion 80 having first and second diametrically opposed mating portions 80a, 80b. The recess 80 is formed with a circular shoulder below the portions 80a, 80b for enabling insertion of the tabs into the portions 80a, 80b and, with a quarter turn, enabling locking of the parts together.

Referring to FIGS. 1 and 3, it can be seen that, with the cleaner 12 coupled to scope 14, the distal end 18 of the tubular sleeve 72 terminates in proximate relation to the light entrance or distal end of the fiberoptic member 16 of the scope 14. In actuality, as shown in FIG. 5, the distal end 18 of the sleeve 72 and its end wall extend slightly beyond the distal end of fiberoptic member 16 by a suitable distance, e.g., five to ten thousandths of an inch in some embodiments, and is provided with an aperture 42 aligned with fiberoptic member 16 such that viewing of the desired area through member 16 and the aperture in the end well of sleeve 72 is accomplished. The inner diameter of the sleeve 72 is slightly greater than the outer diameter of fiberoptic member 16, with the coupling between coupling members 77 and 80 resulting in the sleeve 72 being in generally concentric relation to the fiberoptic member 16. Absolute concentricity is not necessary and, in fact, will not always occur, that is, the distal end 18 of the scrubber tube 72 will have some play relative to the distal end of the member 16.

In operation, with the cleaner 12 attached to the scope 14, the surgeon inserts the apparatus into a slight incision or natural orifice toward the area under observation. The surgeon, or the assistant, then actuates the syringe, via the on/off switch 90 and the control knob 92. The control knob 92 determines the frequency of the aspiration and irrigation cycle through the cleaner 12. The duration of each pulse is pre-set and is not affected by the control knob 92. Alternatively, a foot-pedal or similar activating device can be used to activate the syringe, in which case the cleaner is operated manually rather than automatically.

Figure 4:
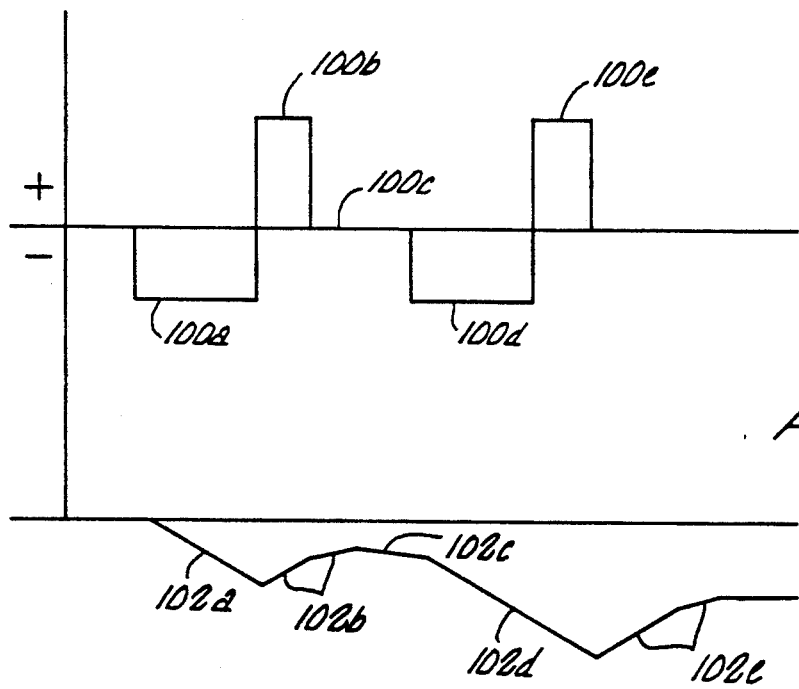
FIG. 4 is a pulse timing diagram of the actuation pulses to the syringe actuator of the scrubber apparatus of FIG. 1 with the pulses correlated to distance of movement of the plunger of the syringe; the relative size of these pulses are exaggerated for purposes of illustration, as will be explained hereinafter.

Referring to FIG. 4, there are shown upper and lower graphs 100 and 102, the upper graph 100 depicting the pulses applied by the stepper motor 30 to the syringe actuator 10, with the lower graph 102 depicting, in time sequence, the physical displacement of the plunger 39 in response to the movement of the stepper motor actuator 35. In graph 100, the first pulse is a negative pulse, designated 100a, which for the purposes herein drives the stepper motor plunger actuator 35 downwardly (as viewed in FIG. 1) to discharge a portion of the cleaning fluid 60 via tubing 62 and annular passage 74 to irrigate the area in proximity to the scope lens at the distal end of fiberoptic member 16. This downward movement of the syringe plunger is depicted by portion 102a of graph 100. The pulse is then followed by a second positive pulse depicted by portion 100b, which retracts plunger 39 at two different rates, first quickly and then more slowly, as depicted by curve 102b which has two slopes, to withdraw a portion of the solution discharged during the previous pulses. This is then followed by a quiescent period depicted by portions 100c and 102c, during which there is no movement of plunger second like cycle follows thereafter as depicted by the negative pulse of portion 100d, resulting in syringe movement 102d, which is then followed by a positive pulse 100e with corresponding movement of syringe plunger 39 as depicted by portion 102e which has two slopes. Alternatively, a single fast aspiration of longer duration may be found suitable. Thus, both irrigation and aspiration are accomplished through the single annular opening 74 provided between the interior of sleeve 72 and the exterior of fiberoptic member 16, and provide a simple, uncomplicated and effective scope cleaning apparatus.

The pulses and timing shown in FIG. 4 are illustrative and the relative sizes of the pulses has been exaggerated to better illustrate the invention. The timing may vary in accordance with factory settings and in accordance with the position of the control knob 94. In any event, the primary purpose of the actuation of the stepper motor actuator 35 is to provide lens cleaning first by irrigation with an ample amount of solution 60, followed by aspiration of a smaller amount of the solution. This is demonstrated by the period or width of the irrigation pulse 100a being larger than the period or width of the aspiration pulse 100b. In actual practice, the difference in size between the irrigation an aspiration pulses will usually be smaller than shown in FIG. 4, but this difference has been exaggerated in the figure to facilitate appreciation of this aspect of the invention. The timing of the irrigation and aspiration pulses is set such that during aspiration, which quickly follows irrigation, the solution in proximity to the lens at the distal end of fiberoptic member 16 will be substantially sterile, thus negating the possibility of any significant amount of debris being returned into the body of the syringe 40. After complete discharge of the solution 60 from within the body of the syringe 40, the plunger 39 may then be withdrawn by actuation of a return switch 94 on the syringe actuator 10, following which another syringe 40 may be attached.

The various parts of the cleaner 12 may be formed of any suitable material, such as surgical stainless steel, which permits sterilization and reuse.

While there has been shown and described a preferred embodiment, it is to be understood that various other adaptations and modifications may be made within the spirit and scope of the invention.

What is claimed is:

1. Apparatus for cleaning a lens end of a surgical scope device having optical means within and elongate optical device with the lens at a distal end thereof, said apparatus comprising:

an elongate sleeve member having an internal transverse dimension slightly greater than the outer transverse dimension of said elongate device and an aperture at the distal end thereof which is in substantial alignment with said lens;

means for coupling said sleeve member in generally concentric relation about said elongate device for defining a single fluid flow passage, said sleeve member when thus coupled having a length sufficient to enable the distal end thereof to terminate beyond, but in proximate relation to said lens; and means for passing solution through said passage in a first direction for enabling removal of debris from the vicinity of said lens and for withdrawing a part of said solution in the opposite direction through said passage;

wherein said means for passing solution includes syringe means for pressurizing said solution; said syringe means is received within a syringe actuator including means for retaining said syringe means therein;

wherein said syringe actuator includes a stepper motor, and means for cyclically actuating said stepper motor in first and second directions and means for actuating a plunger of said syringe means;

wherein said cyclical actuation means of said stepper motor actuates said syringe means to pass a greater volume of said solution in said first direction than is withdrawn into said syringe means in said second direction, such cyclical actuation means being timed such that the duration of a pulse in said first direction is of sufficiently long duration such that substantially all of the debris in the vicinity of said lens is removed and such that substantially debris-free solution is withdrawn into said syringe means during a pulse in said second direction.

2. Apparatus for cleaning a lens end of a surgical scope device having optical means within an elongate optical device with the lens at a distal end thereof, said apparatus comprising:

an elongated sleeve member having an internal transverse dimension slightly greater than the outer transverse dimension of said elongate device and an aperture at the distal end thereof which is in substantial alignment with said lens;

coupling means for attaching said sleeve member in generally concentric relation about said elongate device for defining a generally annular fluid flow passage, said sleeve member when thus coupled having a length sufficient to enable the distal end thereof to terminate beyond, but in proximate relation to said lens;

means on said coupling means for enabling attachment of tubing thereto for enabling flow of solution through said flow passage;

syringe means for pressurizing said solution coupled to said tubing;

means for actuating said syringe means to pass said solution from said syringe means through said flow passage in a first direction enabling removal of debris from in front of said lens and to withdraw a part of said solution in a second direction into said syringe means through said flow passage;

wherein said actuating means includes;

frame means defining an opening for frictionally receiving said syringe means therein;

a stepper motor in engagement with a plunger of said syringe means; and 'control means for actuating said stepper motor in said first direction for a first period and for actuating said stepper motor in said second direction for a second period wherein said first period is greater than said second period such that the duration of said first period is sufficiently long to remove substantially all of the debris in the vicinity of said lens and such that said second period results in substantially debris-free solution being withdrawn into said syringe means.

3. The apparatus according to claim 2 wherein said frame means includes laterally opposed elongate frame members having inner facing edges thereof for receiving said stepper motor therein at one end thereof and for captively retaining said syringe means while enabling movement of said plunger of said syringe means in response to actuation of said stepper motor.

4. A method for removing debris from the vicinity of the lens end of a surgical scope device having optical means within an elongate device, said method comprising:

defining a single generally annular fluid flow passage about the elongate device with an aperture in proximate relation to said lens;

passing solution through the passage in a first direction to remove debris from the vicinity of the lens;

withdrawing part of the solution passed in the opposite direction through the passage;

wherein said steps of passing and withdrawing include actuating a plunger of a solution filled syringe means for pressurizing the solution in first and second directions; and wherein the acutation of the syringe means includes actuating the plunger of the syringe means in the first direction a distance greater than acutating the plunger of the syringe means in the second direction such that substantially all of the debris in the vicinity of the lens is removed from the vicinity of the lens when the solution is passed in the first direction and such that substantially debris-free solution is withdrawn into the syringe means when the solution moves in the second direction.

* * * * *